United States Patent [19]

Pospelova et al.

[11] Patent Number: 5,711,948
[45] Date of Patent: Jan. 27, 1998

[54] PLANT-DERIVED, BIOLOGICALLY ACTIVE POLYSACCHARIDES AND METHOD OF PREPARING SAME

[76] Inventors: Olga L. Pospelova, Ul. Aivazovskogo 6-1-497; Anatoly G. Grizenko, 1st Vrazhsky Per. 4-43; Valery V. Soloviev, Ul. Snaiperskaya S-52; Andrey I. Kozhushkov, Ul. Aivazovskogo 6-1-497; Mikhail N. Starikov, Profsoyuznaya Ul. 29-1-47, all of Moscow, Russian Federation

[21] Appl. No.: 654,545

[22] Filed: May 29, 1996

[51] Int. Cl.[6] ............................................. A61K 35/78
[52] U.S. Cl. ........................................................ 424/195.1
[58] Field of Search ........................................ 424/195.1

[56] References Cited

U.S. PATENT DOCUMENTS 4,469,685  9/1984  Kojima et al. ................. 424/195.1

FOREIGN PATENT DOCUMENTS 833253  5/1981  U.S.S.R. .

*Primary Examiner*—Chhaya D. Sayala
*Attorney, Agent, or Firm*—Cesari and McKenna, LLP

[57] ABSTRACT

Novel plant-derived, biologically active polysaccharides are prepared by grinding a raw material such as young root sprouts *Solanum tuberosum* of a family Solanaseae, extracting with water, incubating at 20° C. for 16–18 hrs, separating the supernatant, incubating the supernatant for at least 20 days, fractionating the supernatant by molecular weight, and concentrating and preparing a dry substance.

11 Claims, No Drawings

PLANT-DERIVED, BIOLOGICALLY ACTIVE POLYSACCHARIDES AND METHOD OF PREPARING SAME

FIELD OF THE INVENTION

The present invention relates to pharmaceutical preparations, and in particular to plant-derived polysaccharides suitable for the treatment and prophylaxis of viral and bacterial infections in mammalian species.

BACKGROUND OF THE INVENTION

Many research groups in different parts of the world have pursued the development of new pharmaceutical preparations for treatment of various viral and bacterial infections. Particular attention is being paid to a search for biologically active compounds of plant origin. This is largely because such compounds generally do not produce toxic reactions and other side effects when introduced into a subject's body.

U.S.S.R. Patent No. 833253, for example, describes a method of preparing a plant-derived biologically active polysaccharide by grinding the raw material (that is an above-soil part of the stem of a leguminous plant (Leguminosae)), boiling, extracting with water at 20° C. for 16–18 hrs, concentrating the extract to the specific density of 1.04–1.06, precipitating with ethyl alcohol (diluted to a water:alcohol ratio of 1:2.5 to 1:6.0), and drying at 50°–60° C.

U.S. Pat. No. 4,145,415 describes a method of isolating three physiologically active compounds by extraction of *Ganoderma lucidum* (Fr.) Karst with boiling water, concentration of the water extract under low pressure, and treatment of the resulting condensate with organic solvents.

U.S. Pat. No. 4,469,685 describes a method of preparing a compound possessing an interferon-inducing activity. The compound can be isolated from various parts of plants of various families by extracting of the raw material with water, salt solutions, or buffer solutions, fractionating of the resulting supernatant, preparing the principal mass of the interferon-inducing compound using ethyl alcohol, and preparing the substance by lyophilization or by chromatography. In this case the extraction is preferably carried out with a ratio of water:plant in the range of 30:1 to 5:1, a pH of 7 to 10, and a temperature range that can vary from room temperature to 120° C. (and is determined by the nature of the raw material); the duration of the extraction process can last up to 5 days. Following extraction, the supernatant is subjected to ultrafiltration, gel sieving chromatography and ion-exchange chromatography, following which the dry compound is prepared.

DESCRIPTION OF THE INVENTION

As a result of extensive research, we found a biologically active, plant-derived polysaccharide that possesses antiviral and antibacterial activity and is contained in young root sprouts of tuber *Solanum tuberosum*. We also developed a method for its isolation from the plant source.

The method of preparing the plant-derived biologically active polysaccharide comprises grinding the raw material; extracting with water; subsequently incubating at 20° C. for 16–18 hrs; separating the extract; and then concentrating and preparing the dry substance. In accordance with the invention, young root sprouts of the tuber *Solanum tuberosum* of the Solanaseae family are used as a raw material, extraction is performed with boiling water or water having a pH ranging from 4.5 to 6.5, the extract isolated by separation is subjected to incubation for not less than 20 days in the presence of conserving compounds (for example, $NaN_3$ in a final concentration of 0.01–0.05%), and before concentration, the material is fractionated by its molecular weight in order to exclude low-molecular weight fractions containing compounds having molecular weights below 50,000 daltons.

The method is performed as follows. Germinating potato tubers are used as a raw material. (To prepare approximately 200 mg of the final product, about 1 kg of the sprouts is required.) Therefore, the final product is prepared from the "awakened plant", that is, from the most actively developing part of the plant, rich in enzymes and nutrients, so that the final product will acquire the highest antiviral and antibacterial activity.

The raw material is preferably ground; for optimization of the extraction process and the maximum recovery of the active principle from the plant source, the material should be reduced to a mush-like state. A homogenizer, such a meat-grinder, can be used for this purpose. The ground material is extracted with boiling water at a water:material ratio of 1:1 to 2:1, and incubated (macerated) at 20° C. for 16–18 hrs. Unlike the prior art, the present invention avoids heating following extraction with boiling water. This, it has been found, promotes better recovery of the active principle and avoids deterioration of the natural properties of the sprouts. The raw material of the invention is available in large quantities and makes the process cost-effective (in fact, byproducts of potato storage can be used as the raw material). A collection of the raw material to be treated as described herein can be started approximately two months after potatoes are put up for storage. Under these conditions, the plant is dormant. After 45–60 days, however, tubers will "awaken" and begin to form sprouts. This approach faciliates collection of sprouts continuously, all year along, without interruption of the ability to practice the invention.

The extract obtained in accordance with the invention is separated by filtration to solid and liquid phases. A press, such as those used in juice-making processes, can be employed to carry out this step. The extract thus obtained is incubated in water at 20° C. for not less that 20 days, which leads to accumulation of a mass of the final product without loss of its biological activity. An exact mechanism of the accumulation of the active principle is not clear as yet. It has been found, however, that a decrease of the incubation time to less than 20 days decreases quantitative yield of the final product. An upper limit for the incubation is not specified since it is determined primarily by convenience in preparing the final product within a given time. An optimal incubation time is 30–40 days.

Following incubation, the extract is fractionated with respect to molecular weight, the primary purpose being to exclude low-molecular weight fractions (mainly up to 50,000 daltons), e.g., by gel-sieving chromatography or ultrafiltration. For a gel-sieving chromatography, a carrier such as Sephadex G-25 or G-50 (commercial products supplied by Pharmacia Fine Chemicals AB, Sweden) or other carriers with similar characteristics can be used; the carrier should resolve the extract into two products: a component containing fractions having molecular weights below about 50,000, and a component containing fractions having molecular weights above about 50,000. The former product is removed.

Ultrafiltration can be performed using membranes, for example, PM-10 (a commercial product supplied by Amicon Corp., USA) or cartridges for hemodialysis such as DIACAP H120 (a commercial product by supplied by B. Brown Melsungen AG, Germany), Fresenius F-40, 60, or 80 (commercial products supplied by by MTS Medizin-Technische Systeme GmbH, Germany), or model 23-08 (a commercial product supplied by Baxter Healthcare Corp., USA), that also provide the extract separation as indicated above.

We have found that hemodialysis cartridges provide the most preferable mode of purification from the perspectives of process velocity and ultimate volumes of the purified extract. These cartridges were utilized as follows. A peristaltic pump, a cartridge described above, and a manometer were connected sequentially, and a closed system was formed by connecting a hose from the cartridge outlet back to the reservoir containing the extract (and from which the extract was pumping into the cartridge inlet). An extra pressure was created in the cartridge's capillaries by a slight tightening of the hose at the cartridge outlet. The pressure was monitored using the manometer, and maintained in the range of 1.2–1.5 atm. (18–22 psi). An additional reservoir was used to collect a solution with low-molecular compounds from the side outlet of the cartridge. During the process, distilled water was added several times to dilute the purifying extract. The purification process was terminated when analysis of fractions from the side outlet of the cartridge indicated the presence of water only. Following this, the product having the predetermined molecular weight was concentrated (for example, by evaporation under vacuum or by ultrafiltration, as described above). The procedure described herein excludes fractions containing low-molecular-weight compounds, ballast compounds, and plant-derived pigments, thereby decreasing the toxicity of the final product.

The final step of the method of the invention is preparing the dry substance, for example by lyophilization (i.e., the freeze-evaporation of water in a vacuum) or by precipitation with ethanol.

Though the physicochemical properties of the active principle have not as yet been fully studied, it appears that the isolated, amorphous, odorless powder, having a light-grey color, is a plant-derived, high-molecular-weight polysaccharide, that easily dissolves in water and water solutions (e.g., a physiological solution of 0.9% NaCl, or a glucose solution), and does not dissolve in ethanol, methanol, chloroform, ether, or acetone. The active principle contains the following monosugars (%): rhamnose, 2.0–10.0; arabinose, 3.0–15.0; xylose, 0.1–3.0; mannose, 0.1–5.0; glucose, 10.0–67.0; galactose, 2.5–27.0; uronic acids, 2.0–5.0 (the wide range of monosugars content can apparently be explained by differences in soil and climate conditions where the plants were growing). The following elemental composition (%) was observed: carbon, 39.95–44.41; hydrogen, 5.17–7.20; nitrogen, 0.1–1.1. The melting point could not be measured, since at 275° C. the product is decomposed. Infrared spectroscopy in a characteristic range of wavelengths showed maxima (polystyrene as a standard) at: 1560, 1610, 1655, 1720. The diffraction coefficient ($nD_{20}$) of a 5%-solution is 1.3394±0.0004.

EXAMPLES

Some examples of the preparing of the plant-derived biologically active polysaccharides are given below. The same amount of the raw material was used in all of the described examples: 1 kg of potato sprouts with length of 15–20 cm and thickness of 0.6–0.8 cm. The sprouts were washed, excess of moisture was removed, the sprouts were ground to a mush-like substance, boiling water was added in the ratio of 1:1 (Example 1) and 1:2 (Example 2). The resulting mass was incubated at 20° C. for 16–18 hrs. The extract obtained was separated into a solid and liquid phases.

Example 1

The extract (1 liter) obtained by separation was subjected to incubation in water at 20° C. for 20 days. The extract was then fractionated according to molecular weight by ultrafiltration through a PM10 membrane, and the dry substance was prepared by freeze-drying in a vacuum. Yield of the product was 215 mg.

Example 2

The extract (1 liter) obtained by separation was subjected to incubation in water at 20° C. for 40 days and then fractionated according to molecular weight using the cartridge Fresenius-80. As described above, the process was performed in a closed-cycle regime. When the volume of the extract was decreased to about 200 ml, the extract was diluted with distilled water to 1 liter. This procedure was repeated 57 times on average. The solution that passed the capillaries was collected separately and the content of low-molecular-weight compounds analyzed. The purification process was repeated as long as low-molecular-weight compounds were detected in the flow-through fractions. The purified extract was then concentrated and dried by lyophilization. Yield of the light-grey powder was 243 mg.

Example 3

The sprouts (1 kg) were washed, excess moisture was removed by leaving the sprouts in an open space for 1–2 hrs, the sprouts were ground, and 2 liters of water brought to pH 4.5 with 1M HCl was added. The mass was stirred. All the follow-up procedures were repeated, as in Example 2. A light-grey powder was obtained, with a mass of 257 mg.

BIOLOGICAL ACTIVITY

The biological activity (in particular, therapeutic activity) of the preparations prepared in Examples 1, 2, and 3 was estimated using models of spontaneous viral and bacterial infections, and also using experimental animals infected with various types of both DNA and RNA containing viruses.

Experiment 1

The compounds prepared in Examples 1 and 2 were used for treatment of hepatitis (Adenovirus family) in 22 dogs by a duplicate subcutaneous injection; for treatment of plague (Paramixovirus) in 30 dogs by a single intravenous and a single subcutaneous injection; and as an antibacterial substance applied on an upper gum infected by staphylococcus. The dogs were of various breeds, gender, and ages. The diagnosis was established on the basis of clinical manifestations and verified by laboratory investigations (e.g., electron microscopy of feces). For subcutaneous and intravenous injections, a dry substance was dissolved in a physiological solution in the concentration of 0.004% to 0.01% (although any other concentration of the compound up to 1.0% can be used if convenient), and the solution was sterilized. A single therapeutic dose for dogs was 0.005–0.1 mg/kg.

In plague cases (Paramixovirus) the cure efficiency was higher than 80%, whereas in the control group of animals the death rate was higher than 70%. In hepatitis cases (Adenovirus) the percentage of animals that recovered following treatment in accordance with the invention was 95%, whereas after treatment by traditional methods it did not exceed 60%. Moreover, the treatment as described in this invention led to a significant shortening of the duration of sickness and to an accelerated cure of the animals.

Experiment 2

15 newborn calves were kept in a farm during a fall-winter season (that is, lower temperature, shorter daylight time, lower amount of fresh fodder). Typically, calves born during this season experience, from birth to an age of about 2 weeks, certain gastrointestinal infections caused by Salmonella, Proteus, and E. coli. When sick, calves lie, refuse to eat, suffer from intractable diarrhea, and exhibit high temperatures. The death rate for calves so afflicted sometimes amounts to 20%. The preparation of the present invention was injected subcutaneously when the first signs of infection were observed; the dose was 0.002–0.005 mg/kg, and after 24–48 hrs the injection was repeated. None of the animals in the treated group died, and these animals exhibited a faster recuperation than the untreated animals; on the average, a treated animal reached its physiological norm 2–3 times faster.

Experiment 3

The animals, their maintenance, the season of birth, and the infection causes were the same as in Experiment 2. Calves were 45–60 days of age. An experimental group contained 7 calves, both males and females. The composition of the present invention was injected subcutaneously when the first signs of infection were observed (diarrhea, elevated temperature, refusal to eat). In as short a time as a few hours, positive signs of recuperation were observed, and after 24 hrs clinical signs of the sickness completely disappeared. Along with the injected compositions, the calves received abundant liquids (including boiled broths) to drink.

The biological activity of the plant-derived polysaccharide of the present invention was also estimated in the context of experimental infection of laboratory animals by viruses of tick-borne encephalitis (Flavivirus, family Togaviridae) and influenza (Orthomyxovirus); herpetic encephalitis (Herpesvirus); Adenovirus; and rabies street virus (Rhabdovirus).

White outbred mice, weighing 8–10 g and 12 g, were infected with tickborne encephalitis virus. The control and experimental groups each contained 25 mice. As a source of the virus (Flavivirus) the "Sol'in" strain was employed in the form of a 10% brain suspension from suckling mice. A viral dose of 5–10 $LD_{50}$ in 0.2 ml was utilized for the infection experiments. The dose was injected subcutaneously, and the pathogenic action of the virus was determined in a dynamic regimen based on the manifestation of clinical symptoms for tick-borne encephalitis, culminating in animal death. The plant-derived compound described in this invention was introduced intravenously into a tail lateral vein at a dosage of 0.1–10.0 mg/kg. The animals were then observed for 30 days.

Experiment 4

Tests were performed using a model for an acute viral infection. White outbred mice weighing 8–10 g were infected with 5–10 $LD_{50}$ subcutaneously. The plant-derived compound of the present invention was introduced in duplicates: after 24 and 72 hrs after the infection by doses in the indicated range. The investigations performed indicate that the compound provides a reliable protection for 33.3% of the mice, while the average duration of the incubation period increased up to 24 hrs.

Experiment 5

The same virus as in Experiment 4 was used, but in this case the course of a subacute viral infection was studied. White outbred mice weighing 12 g were employed for this experiment. The preparation described in this invention was introduced as a single dose of 0.1–2.0 mg/kg 24 hrs after infection, and in duplicate (the same dose) 24 and 96 hrs after the infection. In the control group 26% of the mice died by the end of the observation period, while in the group of the animals that received the preparation described in this invention only 5% died. By the eighth day following infection the brains of 5 mice from each group were removed. 10% brain suspensions were prepared therefrom and titrated in cell cultures of kidney pig embryo (a sensitive cell line for reproduction of the tick-borne virus). The data obtained indicate that, for the animals receiving single and duplicate doses of the preparation of the present invention, titers of the tick-borne virus in the brain of infected animals were 2.5–3.0 lg lower than those for the control animals for the observation period.

The observations in all of the examples described herein indicate that introduction of the present preparation, in single and duplicate doses in the range of 0.001 mg/kg to 10.0 mg/kg, did not produce changes in the animals in terms of behavior, growth, mobility, or appearance, indirectly indicating a lack of toxicity.

A toxicity study of the new plant-derived biologically active polysaccharide was performed in accord with the following National Judicial Requirement of Russia: (i) Requirements for Clinical Studies of the General Toxic Action of New Pharmacological Compounds, Federal Pharmacological Committee of the Ministry of Health (FPCMH), Moscow, Russia, 1985; (ii) Evaluation of a Mutagenicity of New Medicinal Agents, FPCMH, Moscow, Russia, 1992; (iii) Methodological Directions on Studies of the Embryotoxic Action of Pharmacological Compounds and their Effect on the Reproductive Function, FPCMH, Moscow, Russia, 1986; and in accord with the requirements of the International Committee on Economics with respect to Studies on New Pharmacological Compounds, CE, 1984.

Our studies demonstrate that the compositions of the present invention are related to a group of low-toxicity compounds: $LD_{50}$ for the intravenous introduction to male mice is 1075 mg/kg; the compound in therapeutic doses does not effect the hematological indications, blood clotting, protein and lipid metabolism, and the antitoxic liver function; and it does not produce embryotoxic, teratogenic, or mutagenic effects. The compound in the dry form retains its activity when stored for long periods of time; the compound dissolved in water, physiological solution and similar solutions appropriate for injections in sterile conditions, retains its activity without any changes for at least 5 years (the period of our experimental observations). The compound can easily be used in various medicinal formulations: in solutions, as described above, for injections (e.g., intravenous, intraperitoneal, intramuscular and subcutaneous); as creams and ointments; as a constituent of special medicinal films and coatings for prolonged introduction into a body; as suppositories for vaginal and rectal introductions (for example, on a base of cocoa butter); as aerosols, sprays, and nasal and eye drops; for topical applications; and any similar medicinal forms.

Experiment 6

The counter-infectious activity of the plant-derived preparations described herein was studied on human volunteers, 10 males and 10 females, between 18 and 45 years of age. All patients showed ureteropathy and genital infections. Using vaginal and male urethral smears, the immunofluorescent detection identified the cause of the infection as *Chlamydia trachomatis*. The patients were treated by a duplicate intravenous injection with the preparation of the present invention on the first and third day of the treatment. The preparation was dissolved in physiological solution (0.9% NaCl in distilled water), sterilized, and injected as a 0.001–0.003 mg/kg dose. On the second, fourth and fifth day of treatment the preparation was introduced as a suppository, rectally for males and rectally or vaginally for females; suppositories were introduced one piece at a time before a night's sleep. The suppositories were prepared on a base of cocoa butter, each containing 100 mkg of the active compound. Two weeks after the final introduction of the preparation (that is 19–20 days after the beginning of the treatment), control smears were taken from the vagina and the urethra. It was observed that 17 patients (i.e., 85% of the total) were completely cured from *Chlamydia trachomatis*. Another 3 patients (15%) bore *Chlamydia trachomatis* that showed morphological changes, as observed by laboratory studies. Conventional treatment of these patients using antibiotics has resulted in 100% success in cure of the indicated ureterogenital infection.

These results, we believe, demonstrate the feasibility of treating a number of different viral and bacterial infections in humans. This is particularly significant in view of the fact that treatment of such a known viral disease as, for example, Herpesvirus, is complicated by an acquired resistance of humans to Acyclovir, a conventional medication for this infection; treatment of influenza is complicated by an appearance of a remantadine-resistant strain; and treatment of the above-described chlamydia-type infection is sometimes subverted by an acquired resistance to antibiotics. Moreover, treatment of humans with antiviral and antibacterial preparations is often accompanied by a number of unwanted side effects.

The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. A method of preparing a biologically active polysaccharide, the method comprising the steps of:
    a. obtaining a tuberous root sprout of *Solanum tuberosum*, family Solanaseae;
    b. grinding the root sprout;
    c. extracting with water to produce an extractant;
    d. incubating the extractant; and
    e. fractionating the extractant to exclude species having molecular weights less than about 50,000 daltons, thereby isolating a polysaccharide having a molecular weight of at least 50,000 daltons.

2. The method of claim 1 further comprising the step of concentrating and processing the extractant into a dry substance.

3. The method of claim 1 wherein the extraction step comprises pouring hot water on the ground root sprout, stirring, and incubating to produce a mass, and then incubating the mass at 20° C. for 16–18 hours.

4. The method of claim 1 wherein the extractant is incubated for not less than 20 days in the presence of an antiseptic compound.

5. The method of claim 2 wherein the processing step comprises lyophilization.

6. A composition comprising a polysaccharide having a molecular weight of at least 50,000 daltons, the composition being prepared from *Solanum tuberosum*, family Solanaseae according to steps comprising:
    a. obtaining a tuberous root sprout of *Solanum tuberosum*, family Solanaseae;
    b. grinding the root sprout;
    c. extracting with water to produce an extractant;
    d. incubating the extractant; and
    e. fractionating the extractant to exclude species having molecular weights less than about 50,000 daltons.

7. The composition of claim 6 wherein fractionated extractant is concentrated and processed into a dry substance.

8. The composition of claim 6 wherein the extraction step comprises pouring hot water on the ground root sprout, stirring, and incubating to produce a mass, and then incubating the mass at 20° C. for 16–18 hours.

9. The composition of claim 6 wherein the extractant is incubated for not less than 20 days in the presence of an antiseptic compound.

10. The composition of claim 6 wherein the processing step comprises lyophilization.

11. A method of preparing a biologically active composition, the method comprising the steps of:
    a. obtaining a tuberous root sprout of *Solanum tuberosum*, family Solanaseae;
    b. grinding the root sprout;
    c. extracting with water to produce an extractant by pouring hot water on the ground root sprout, stirring, and incubating to produce a mass, and then incubating the mass at 20° C. for 16–18 hours;
    d. incubating the extractant for not less than 20 days;
    e. fractionating the extractant to exclude species having molecular weights less than about 50,000 daltons; and
    f. isolating an active principle having a molecular weight of at least 50,000 daltons.

* * * * *